United States Patent [19]

Tvrtkovic-Sahin et al.

[11] Patent Number: Plant 7,397

[45] Date of Patent: Dec. 18, 1990

[54] ASTER PLANT NAMED WHITE BUTTERFLY

[76] Inventors: Zelimir K. Tvrtkovic-Sahin, Barnsteenstraat 24, 2403 BZ Alphen aan den Rijn; Petrus J. Akerboom, Paradijsweg 61, 2461 TL Ter Aar, both of Netherlands

[21] Appl. No.: 378,178

[22] Filed: Jul. 11, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

An Aster plant named White Butterfly particularly characterized by its cupped capitulum form; daisy capitulum type; white ray floret color; diameter across face of capitulum of 34 to 35 mm at maturity; strong, well branched flower stems; and many capitula per inflorescence on short pedicels.

1 Drawing Sheet

1

The present invention comprises a new and distinct cultivar of Aster plant, hereinafter referred to by the cultivar name White Butterfly.

White Butterfly is a product of a planned breeding program which had the objective of creating new perennial Aster cultivars for year-round commercial production having well branched flower stems, good flower size, good flower form, and having superior lasting quality of the cut flowers. Such traits in combination were not present in previously available commercial cultivars.

White Butterfly was originated from a hybridization made by the inventors K. Sahin and P. Akerboom in a controlled breeding program in Ter Aar, The Netherlands, in 1984. The female parent of White Butterfly was *Aster pringlei c.v. Monte Casino.* The male parent was an unnamed *Aster novi-belgii* seedling.

White Butterfly was discovered and selected as one flowering plant within the progeny of the stated parentage by the inventors K. Sahin and P. Akerboom on Sept. 2, 1985 in a controlled environment in Ter Aar, and identified as Seedling No. 84/165.

The first act of asexual reproduction of White Butterfly was accomplished when vegetative cuttings were taken from the initial selection in November of 1985 in a controlled environment in Ter Aar, by a technician working under formulations established and supervised by K. Sahin and P. Akerboom.

Horticultural examination of selected units initiated in 1985 and 1986 has demonstrated that the unique combination of characteristics as herein disclosed for White Butterfly are firmly fixed and are retained through successive generations of asexual reproduction.

White Butterfly has not been observed under all possible environmental conditions. The phenotype may vary significantly with variations in environment such as temperature, light intensity and daylength.

The following observations, measurements and comparisons describe plants grown in Ter Aar under greenhouse conditions which approximate those generally used in commercial greenhouse practice in The Netherlands.

The following traits have been repeatedly observed and are determined to be basic characteristics of White Butterfly, which, in combination, distinguish this Aster as a new and distinct cultivar:

2

1. Cupped capitulum form.
2. Daisy capitulum type.
3. White ray floret color.
4. Diameter across face of capitulum of 34 to 35 mm at maturity.
5. Strong, well branched flower stems.
6. Many capitula per inflorescence on short pedicels.

The accompanying photographic drawing shows typical inflorescence of White Butterfly, with the colors being as nearly true as possible with illustrations of this type. The color photograph is a perspective view of White Butterfly grown as a single stem cut spray Aster.

Of the commercial cultivars known to the inventors, the most similar in comparison to White Butterfly is the female parent Monte Casino. Reference is made to attached Chart A, which compares certain characteristics of White Butterfly to the same characteristics of Monte Casino.

In comparison to Monte Casino, White Butterfly has stronger flowering stems, better branching, more capitula per inflorescence, larger flowers, a greater number of ray florets, and longer lasting quality of the cut flowers. With regard to the last mentioned characteristics, when grown under similar conditions, the blossoms of White Butterfly will last 2–3 days longer than the flowers of Monte Casino. Similar traits are ray floret color, capitulum form and type, spray formation and photoperiodic light reaction.

In the following description color references are made to The Royal Horticultural Society Colour Chart. The color values were determined between 12:00 and 14:00 hours on Mar. 16, 1987 at Alphen aan den Rijn, The Netherlands.

Classification:

*Botanical.*—*Aster pringlei*×*novi-belgii* cv White Butterfly.

*Commercial.*—Small daisy-like spray Aster perennial.

INFLORESCENCE

A. Capitulum:

*Form.*—Cupped.

*Type.*—Daisy.

*Diameter across face.*—34–35 mm.

*Arrangement.*—Raceme inflorescence.

B. Corolla of ray florets:

*Color (general tonality from a distance of three meters).*—White.

*Color (upper surface).*—Closest to 155D.

*Color (under surface).*—Closest to 155D.

*Shape of floret.*—Apex reflexing; narrow, oblon, straight.

*Size of floret.*—14–15 mm long×2 mm wide.

*Number of ray florets.*—29–35.

C. Corolla of disc florets:

*Color (mature).*—Closest to 1C to 1D.

*Color (immature).*—Closest to 1C to 1D.

*Diameter of disc.*—7 mm.

D. Reproductive organs:

*Androecium.*—Present on disc florets only; no pollen.

*Gynoecium.*—Present on both ray and disc florets.

PLANT

A. General appearance:

*Height.*—Medium to tall; depends on light reaction. Under continuous long days it can grow up to 2 meters tall medium branching.

B. Foliage:

*Color.*—147A to 147B.

*Shape.*—Oblanceolate and linear, with occassional downward reflexing at the tip.

*Size.*—99–110 mm long×7–14 mm wide.

*Length.*—Short to medium; width medium to broad.

*Margin.*—Entire.

*Arrangement.*—Alternate, with angle acute.

CHART A
COMPARISON OF WHITE BUTTERFLY AND MONTE CASINO

| Cultivar | White Butterfly | Monte Casino |
|---|---|---|
| Ray Floret Color | White | White |
| Capitulum Form and Type | Cupped daisy | Cupped daisy |
| Spray formation | Compound | Compound |
| Pedicels | 7–22 mm long | 7 mm long |
| Diameter across face of capitulum | 34–35 mm | 20–22 mm |
| Number of ray florets | 29–35 | 27 |

Comparisons made on plants grown as single stem spray Asters in Ter Aar, The Netherlands

We claim:

1. A new and distinct Aster plant named White Butterfly, as described and illustrated.

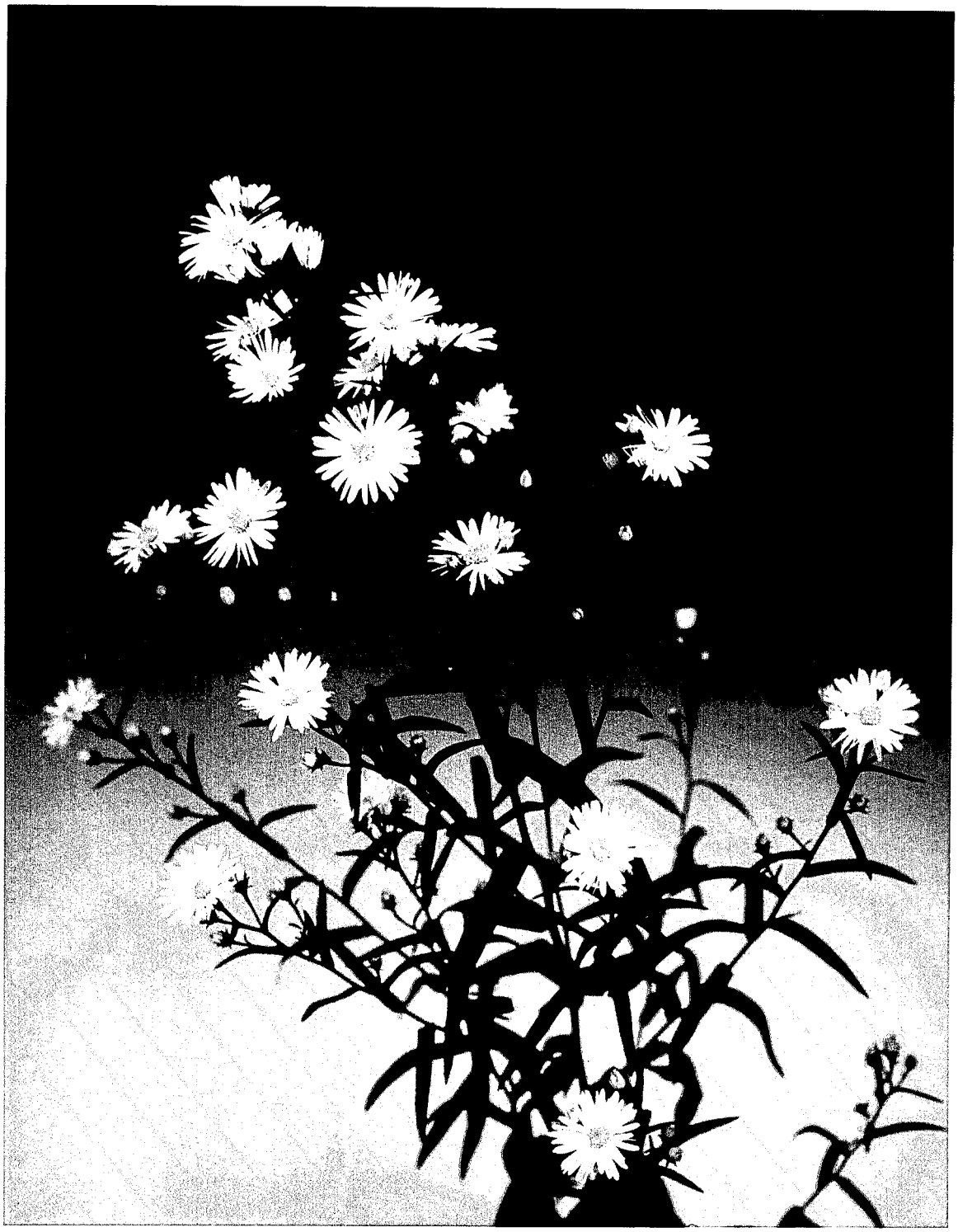

* * * * *